(12) United States Patent
Mondello et al.

(10) Patent No.: US 11,571,126 B2
(45) Date of Patent: Feb. 7, 2023

(54) SECURE WIRELESS COMMUNICATION BETWEEN IMPLANTS AND APPARATUS

(71) Applicant: Micron Technology, Inc., Boise, ID (US)

(72) Inventors: Antonino Mondello, Messina (IT); Alberto Troia, Munich (DE)

(73) Assignee: Micron Technology, Inc., Boise, ID (US)

( * ) Notice: Subject to any disclaimer, the term of this patent is extended or adjusted under 35 U.S.C. 154(b) by 989 days.

(21) Appl. No.: 16/362,976

(22) Filed: Mar. 25, 2019

(65) Prior Publication Data

US 2020/0305716 A1 Oct. 1, 2020

(51) Int. Cl.
| | |
|---|---|
| *A61N 1/00* | (2006.01) |
| *A61B 5/00* | (2006.01) |
| *H04W 4/80* | (2018.01) |
| *A61N 1/372* | (2006.01) |
| *A61B 5/07* | (2006.01) |
| *G06F 12/14* | (2006.01) |

(52) U.S. Cl.
CPC ............ *A61B 5/0031* (2013.01); *A61B 5/686* (2013.01); *A61B 5/6867* (2013.01); *H04W 4/80* (2018.02); *A61B 5/076* (2013.01); *A61N 1/37288* (2013.01); *G06F 12/1408* (2013.01)

(58) Field of Classification Search
CPC ..... A61B 5/0031; A61B 5/686; A61B 5/6867; A61B 5/076; H04W 4/80; H04W 12/069; A61N 1/37288; A61N 1/378–3787; A61N 1/37211–3727; G06F 12/1408
See application file for complete search history.

(56) References Cited

U.S. PATENT DOCUMENTS

| | | | |
|---|---|---|---|
| 8,638,062 B2 | 1/2014 | Baarman | |
| 2001/0023360 A1* | 9/2001 | Nelson | .......... G16H 40/67 607/60 |
| 2009/0063193 A1 | 3/2009 | Barton | |

(Continued)

FOREIGN PATENT DOCUMENTS

| | | |
|---|---|---|
| EP | 2842521 A1 | 4/2015 |
| WO | 2017-160627 A2 | 9/2017 |
| WO | 2017-160723 A1 | 9/2017 |

OTHER PUBLICATIONS

International Search Report & Written Opinion from related International Application No. PCT/US2020/021653, dated Jun. 30, 2020, 13 pages.

(Continued)

*Primary Examiner* — Scott M. Getzow
(74) *Attorney, Agent, or Firm* — Brooks, Cameron & Huebsch, PLLC

(57) ABSTRACT

An apparatus can have a computing component. The computing component can be configured to receive a wireless transmission from an implanted device, verify an identity of the implanted device by verifying security data from the implanted device, and perform an authentication procedure, in response to verifying the identity of the implanted device, to determine whether the transmission is authentic by determining whether a digital signature of the transmission is authentic. The apparatus can be configured to wirelessly charge the implanted device in response to the computing component determining that the digital signature is authentic.

24 Claims, 8 Drawing Sheets

(56) References Cited

U.S. PATENT DOCUMENTS

| 2009/0069868 | A1 | 3/2009 | Bengtsson et al. |
| 2014/0304773 | A1 | 10/2014 | Woods et al. |
| 2017/0127373 | A1* | 5/2017 | Deshpande ......... H04W 64/003 |
| 2017/0173261 | A1 | 6/2017 | O'Connor et al. |

OTHER PUBLICATIONS

U.S. Appl. No. 15/853,498, entitled, "Physical Unclonable Function Using Message Authentication Code", filed Dec. 22, 2017, 28 pages.
U.S. Appl. No. 16/201,652, entitled, "Parking Infrastructure Powered By a Decentralized, Distributed Database", filed Nov. 27, 2018, 27 pages.
U.S. Appl. No. 15/993,119, entitled, "Transmission of Vehicle Route Information By Passive Devices", filed May 30, 2018, 25 pages.
U.S. Appl. No. 16/034,763, entitled, "Secure Vehicular Communication", filed Jul. 13, 2018, 37 pages.
U.S. Appl. No. 16/034,809, entitled, "Secure Vehicular Services Communication", filed Jul. 13, 2018, 36 pages.
PCT International Application No. PCT/IB2019/000089, entitled, "Method for Improving Safety of a Component or System Running a Firmware or a Finite State Machine", filed Feb. 22, 2019, 42 pages.
Patel, Research Article, Journal of Biosensors & Bioelectronics, entitled Wireless Charging of Implantable Pacemaker's Battery, vol. 9, Issue 3, ISSN: 2155-6210, Published Sep. 28, 2018, 2 pages.

* cited by examiner

SECURE WIRELESS COMMUNICATION BETWEEN IMPLANTS AND APPARATUS

TECHNICAL FIELD

The present disclosure relates generally to wireless apparatus and, more particularly, to secure wireless communication between implants and apparatus.

BACKGROUND

Various devices, such as implants, can be implanted into living organisms, such as humans or animals. Some implants can store information about the identity living organism. Some implants can be trackers that can track geographical locations of the living organism. Some implants can be medical devices that can monitor and/or control various functions of the organism, such as heart rate, glucose levels, or the like. Some implants can be medical prostheses that can replace missing or damaged body parts of the living organism.

Since implants can be difficult to access, some implants can be accessed wirelessly by a various remote wireless apparatus. For example, implants and various remote wireless apparatus might communicate wirelessly by exchanging wireless communications (e.g., transmissions). For example, some remote wireless apparatus can receive wireless transmissions that can include data (e.g., information) stored by the implant. In some instances, some remote wireless apparatus might send wireless transmissions to cause an implant to perform various operations in response to the information contained in a wireless transmission.

DETAILED DESCRIPTION

Figure 1:
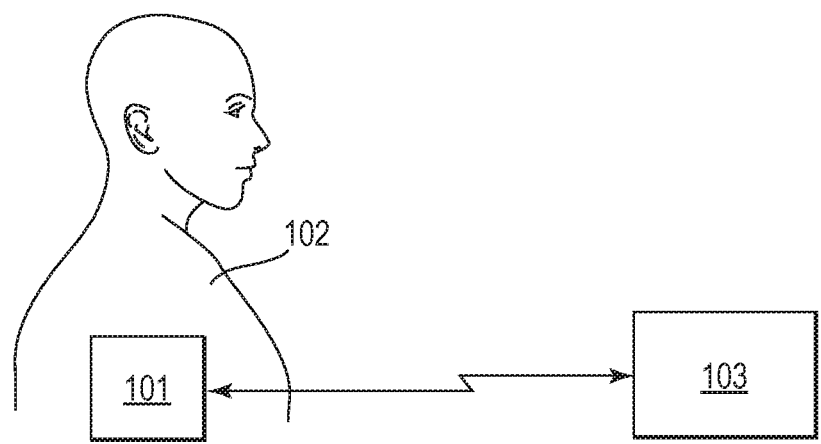
FIG. 1 illustrates a system in accordance with a number of embodiments of the present invention.

Wireless transmissions between an implanted device (e.g., implant) and a remote wireless apparatus can be insecure and can be intercepted and/or manipulated by a hacker or other entities in order to change the wireless transmission, repeat the wireless transmission to gain unauthorized access to the implanted device, and the like. Such unauthorized accesses can have catastrophic consequences to the living organism in which the implanted device is implanted and/or can have a negative impact on the implanted device.

The various embodiments disclosed herein can provide technical advantages over previous approaches by providing for secure communications between a remote apparatus and an implanted device that can guard against such unauthorized accesses. For example, an apparatus, such as a remote wireless apparatus, can have a computing component that can be configured to receive a wireless transmission from an implanted device (e.g., implanted in a living organism). The wireless transmission can have a digital signature. The computing component can be configured to verify an identity of the implanted device by verifying security data from the implanted device, and can perform an authentication procedure, in response to verifying the identity of the implanted device, to determine whether the transmission is authentic by determining whether the digital signature is authentic. For example, the apparatus might not access data that is contained in the wireless transmission unless the computing component verifies security data from the implanted device and determines that the transmission is authentic.

In some instances, implanted devices can be battery powered. However, an implanted device battery can discharge over time and can render the implanted device inoperable. Various previous approaches involved performing surgery to replace an implanted device battery. However, in some instances, such as when a living organism's health is at risk, it might not be possible to perform surgery to replace an implanted device battery. The various embodiments disclosed herein provide technical advantages over previous approaches by avoiding surgery to replace implanted device batteries. For example, various embodiments can avoid surgery by providing wireless chargers that can securely, wirelessly charge the implanted device.

For example, a wireless charger can be configured to authenticate the implanted device to the wireless charger and the implanted device can be configured to authenticate the wireless charger to the implanted device to establish secure communication between the implanted device and the wireless charger. Once the secure communication is established, the wireless charger can accept a secure transmission from the implanted device, indicating that the wireless implant needs to be charged. The secure transmission can be signed with a digital signature and can include security data from the implanted device. The wireless charger can verify an identity of the implanted device by verifying the security data from the implanted device and can wirelessly charge the implanted device in response to authenticating the digital signature and verifying the security data from the wireless implanted device. Establishing secure communication, verifying the identity of the wireless implanted device, and authenticating the digitally signed transmission can guard against unauthorized accesses that can negatively impact the charging process, and thereby provide technical advantages over previous approaches.

FIG. 1 illustrates a system, such as a secure communication system, in accordance with a number of embodiments of the present invention. The system can include a device 101 (e.g., an apparatus), such as a medical device, that can be implanted in a living organism, such as a human 102 or an animal body. For example, device 101 can be referred to as an implanted device and/or implant. In some examples, device 101 can be a heart device, a pacemaker, an artificial heart, a blood device, a pulse device, a prosthesis device, a bone-inserted device, an electronic body part (e.g., a hand, a leg, and/or anything able to retrieve data and having an ability to send data out of the body).

The system can include a remote apparatus 103, such as a charger and/or a monitor, that can be outside of (e.g., external to) human 102 and remote to device 101. In some examples, apparatus 103 can be a wearable that can be worn by human 102, such as on a wrist of human 102. Apparatus 103 can be wirelessly coupled to device 101. Apparatus 103 and device 101 can exchange secure wireless communications, such as transmissions. Secure transmissions can refer to transmissions that require authentication, for example. In some examples, a secure transmission can include data, a digital signature, and a freshness indicator.

Apparatus 103 and device 101 can mutually authenticate to each other using the authentication protocols described herein. The mutual authentication can establish secure communication between apparatus 103 and device 101 can allow apparatus 103 and device 101 to exchange secure wireless transmissions. In some instances, the mutual authentication can occur the first time apparatus 103 is used with device 101. For example, the mutual authentication can occur in response to apparatus 103 being moved to within a particular distance of device 101.

In some instances, apparatus 103 can wirelessly charge device 101 after secure communication is established between apparatus 103 and device 101 and in response to apparatus 203 authenticating a secure transmission from device 101 that indicates device 101 needs to be charged.

Figure 2:
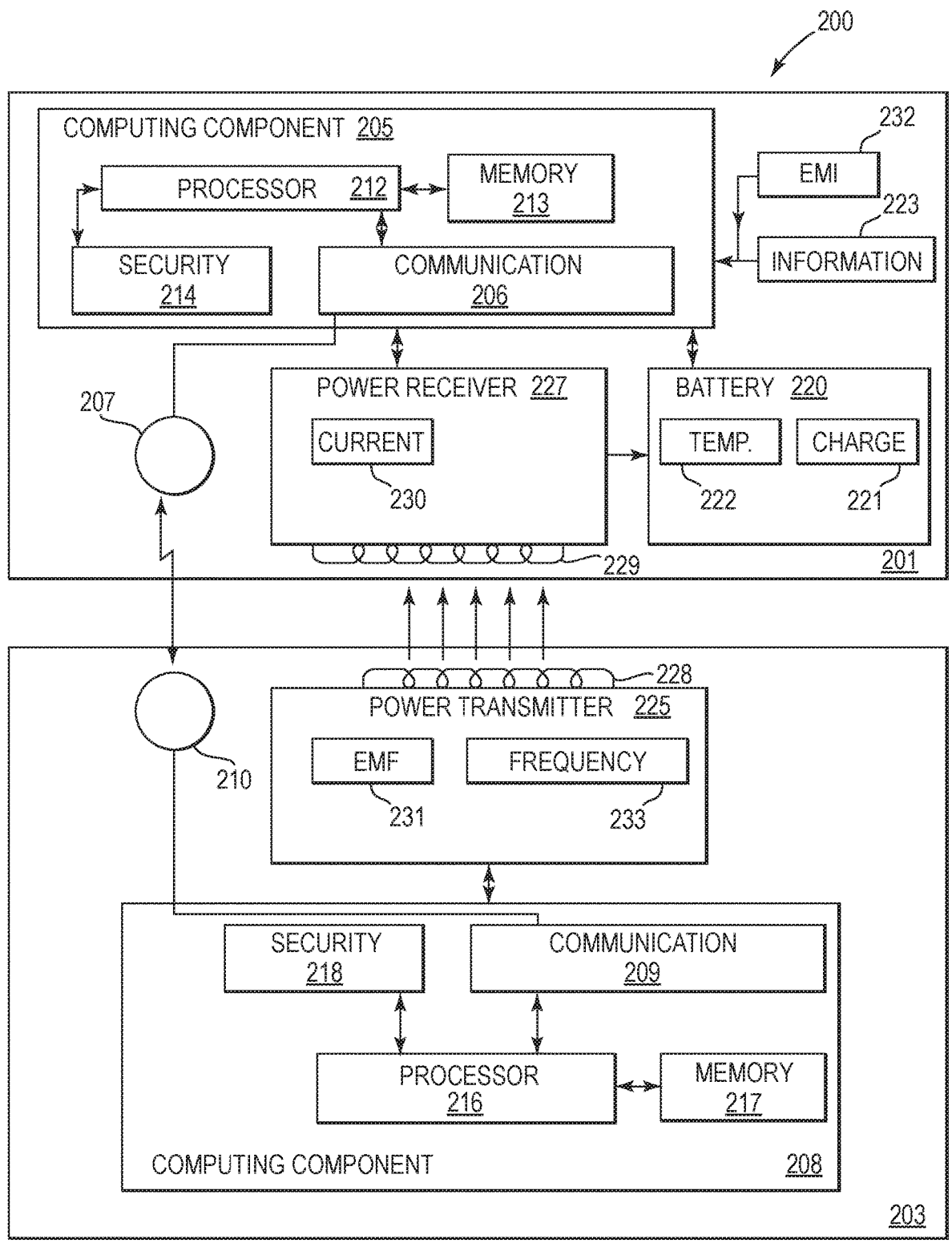
FIG. 2 is a block diagram of a system in accordance with a number of embodiments of the present disclosure.

FIG. 2 is a block diagram of a system 200, such as a medical system, that can be the system discussed in conjunction with FIG. 1, in accordance with a number of embodiments of the present disclosure. System 200 can include a device 201 that can be device 101. For example, device 201 can be implanted in human 102 or an animal body.

An apparatus 203 that can be apparatus 103 can be wirelessly coupled to device 201. For example, apparatus 203 can be external to human 102 and can be a charger configured to charge device 201. In some examples, apparatus 203 can be a monitor that can monitor information about the operation of device 201 and/or information about the functioning of human 102 as a result of the operation of device 201. The information can be included as data in secure transmissions that can be sent to apparatus 203 from device 201.

Device 201 can include a computing component 205 (e.g., control circuitry) that can have a communication component 206. Computing component 206 can be configured to perform the various security operations (e.g., protocols), associated with device 201, described herein. Communication component 206 can be coupled to an antenna 207.

Apparatus 203 can include a computing component 208 that can have a communication component 209. Computing component 208 can be configured to perform the various security operations (e.g., protocols), associated with apparatus 203, described herein. Communication component 209 can be coupled to an antenna 210. Communication components 206 and 209 can facilitate the wireless communications (e.g., the exchange of wireless transmissions) between device 201 and apparatus 203 via antennas 207 and 210.

Computing component 205 can include a processor 212 coupled to communication component 206, to a memory 213 (e.g., a non-volatile memory), and to a security component 214. Although security component 214 is shown as being separate from communication component 206 and memory 213, security component 214 can be integrated in communication component 206 and/or memory 213. For example, security component 214 can include hardware and/or logic that can configure security component 214 to perform the various security operations associated with device 201. In some instances, processor 212 can act as a host to memory 213.

Processor 212 can execute instructions (e.g., firmware), that can be stored in memory 213, to cause security component 214 to perform the various security operations described herein. For example, security component 214 can encrypt and decrypt data, authenticate wireless transmissions received from communication component 209, generate digital signatures, verify digital signatures, generate security data, authenticate device 201 to apparatus 203, generate public and private keys, generate public and private device identifications of device 201, generate a public device identification certificate of device 201, and the like. In some examples, communication component 206 can receive a wireless transmission, with a digital signature, from communication component 209, and security component 214 can verify an identity of device 201 by verifying security data from device 201 and can perform an authentication procedure, in response to verifying the identity of the implanted device, to determine whether the transmission is authentic by determining whether the digital signature is authentic.

Computing component 208 can include a processor 216 coupled to communication component 209, to a memory 217 (e.g., a non-volatile memory), and to a security component 218. Although security component 218 is shown as being separate from communication component 209 and memory 217, security component 218 can be integrated in communication component 209 and/or memory 217. For example, security component 218 can include hardware and/or logic that can configure security component 218 to perform the various security operations associated with apparatus 203. In some instances, processor 216 can act as a host to memory 217.

Processor 216 can execute instructions, that can be stored in memory 217, to cause security component 218 to perform the various security operations described herein. For example, security component 218 can encrypt and decrypt data, generate security data, authenticate wireless transmissions received from communication component 206, generate digital signatures, verify digital signatures, authenticate apparatus 203 to device 201, generate public and private keys, generate public and private apparatus identifications of apparatus 203, generate a public device identification certificate of apparatus 203, and the like. In some examples, communication component 209 can receive a wireless transmission, with a digital signature, from communication component 206, and security component 218 can perform an authentication procedure to determine whether the transmission is authentic by determining whether the digital signature is authentic.

In some examples, communication components 206 and 209 can communicate (e.g., exchange wireless transmissions) using wireless communication protocols, such as a Bluetooth protocol, a radio frequency protocol, among other wireless communication protocols, that can be stored in memories 213 and 217. Processors 212 and 216 can execute the protocols to cause communication components 206 and 209 to communicate wirelessly. For example, processors 212 and 216 can respectively cause communication components 206 and 209 to perform the various wireless communication operations disclosed herein. In some instances, the wireless communication can be initiated in response to antennas 207 and 210 being moved to within a communication distance of each other.

Computing components 205 and 208 can allow secure transmissions to be exchanged between communications components 206 and 209 in response to security components 214 and 218 mutually authenticating device 201 and apparatus 203. For example, security component 214 might authenticate apparatus 203 to device 201 in response to determining that apparatus 203 includes (e.g., memory 217 stores) particular secret data (e.g., a data secret). Security component 218 might authenticate device 201 to apparatus 203 in response to determining that device 201 has (e.g., memory 213 stores) particular secret data.

For example, the particular secret data can be stored in memory 213 during the manufacture of device 201 and the particular secret data can be stored in memory 217 during the manufacture of apparatus 203. In some examples, the particular secret data that can be stored in memory 213 and the particular secret data that can be stored in memory 217 can be the same particular data. For example, the particular secret data can be hidden in secret regions of memories 213 and 217 that cannot be accessed (e.g., addressed) by processors 212 and 216.

A battery 220 can be coupled to computing component 205. In some examples, communication component 206 can send a secure transmission that can include data (e.g., service information) indicative of a charge 221 on battery 220 and/or a temperature 222 of battery 220 to communication component 209. In some examples, communication component 206 can send the secure transmission in response to communication component 206 receiving a secure transmission from communication component 209 including data requesting the service information.

Computing component 205 can receive information 223 about device 201 and/or about human 102, and communication component 206 can send a secure transmission that can include the information to communication component 209. In some examples, such as when the information is sensitive information, security component 214 can encrypt the information, and security component 218 can decrypt the information. In some instances, communication component 206 can send the secure transmission in response to communication component 206 receiving a secure transmission from communication component 209 including data requesting the information.

For examples in which apparatus 203 is a charger, apparatus 203 can have a power transmitter 225. For example, power transmitter 225 can transmit power wirelessly (e.g., via an inductive coupling) to a power receiver 227 of device 201 coupled to battery 220 to charge battery 220. Power transmitter 225 can have coils 228 that can generate an electromagnetic field (EMF) 231 having a frequency 233 in response to current flowing through the coils 228. EMF 231 can be imparted to coils 229 of power receiver 227 and can induce current 230 in coils 229. Current 230 can be used to charge battery 220.

Processor 212 can be coupled to power receiver 227 and can execute instructions, that can be stored in memory 213, to control the operation of power receiver 227 (e.g., to cause power receiver 227 to charge battery 220). For example, processor 212 can execute instructions that cause computing component 205 to control the operation of device 201, such as the operation of power receiver 227. As such processor 212 can control the operation of power receiver 227 and can cause power receiver 227 to perform various charging operations.

Processor 216 can be coupled to power transmitter 225 and can execute instructions, that can be stored in memory 217, to control the operation of power transmitter 225 (e.g., to cause power transmitter 225 to generate EMF 231 with a frequency 233). For example, processor 216 can execute instructions that cause computing component 208 to control the operation of apparatus 203, such as the operation of power transmitter 225. As such, processor 216 can control the operation of power transmitter 225 and can cause power transmitter 225 to perform various charging operations. For example, processor 216 can cause power transmitter 225 to control EMF 231 and/or frequency 233.

Device 201 can have an electromagnetic interference (EMI) detector 232. Computing component 208 can cause power transmitter 225 to adjust a strength of EMF 231 in response to authenticating a secure transmission received at communication component 209 from communication component 206. The secure transmission can include a digital signature and service data that can indicate of the status various charging parameters, such as the status (e.g., the level) of current 230, temperature 222, and/or the EMI detected by EMI detector 232. Computing component 208 can the secure transmission by authenticating (e.g., verifying) the digital signature, as described herein. Computing component 208 can adjust the strength of EMF 231 based on the status current 230, temperature 222, or EMI. In some instances, communication component 206 can send the secure transmission in response to communication component 206 receiving a secure transmission from communication component 209, including data requesting the service data.

Computing component 208 can stop the charging process in response to communication component 209 receiving a secure transmission from communication component 206 that indicates that battery 220 is completely charged, EMI 232 is greater than a threshold level, or information 223 indicates that device 201 has malfunctioned. Note, for example, that excessive battery temperatures can be harmful to human 102 and that excessive EMIs can interfere with the charging process and various functions of human 102.

Communication component 209 can, for example, receive a digitally signed device 201 transmission from communication component 206, indicating that device 201 needs to be charged. Computing component 208 can cause power transmitter 225 to wirelessly charge device 201 in response to security component 218 determining that the digitally signed device 201 transmission is authentic by determining that a digital signature of the digitally signed device 201 transmission is authentic.

In some examples, communication component 209 can send a digitally signed apparatus 203 transmission to communication component 206, requesting information about the level (e.g., amount) of charge on battery 220. Communication component 206 can then send the digitally signed device 201 transmission to communication component 209 in response to security component 214 determining that a digital signature of the digitally signed apparatus 203 transmission is authentic.

In some examples, communication components 206 and 209 can exchange secure transmissions as part of an iterative processes to set a level of an operating (e.g., charging) parameter, such as charge 221, temperature 222, and/or current 230, of device 201. For example, communication component 209 can send a secure transmission, having data requesting the present level of the operating parameter, to communication component 206. In response, communication component 206 can send a secure transmission to communication component 209, having data indicating the present level of the operating parameter. Computing component 208 can cause power transmitter 225 to adjust the operation of power transmitter 225 by adjusting the EMF 213 and/or frequency 233 in response to the present level of the operating parameter being outside of a predetermined (e.g., desired) operating range for the operating parameter.

Subsequently, communication component 209 can send a secure transmission, having data requesting an updated level of the operating parameter resulting from the adjusted EMF 213 and/or frequency 233, to communication component 206. In response, communication component 206 can send a secure transmission to communication component 209, having data indicating the updated level of the operating parameter. If the updated level, lies in the predetermined range the process stops. Otherwise, the process of exchanging secure transmissions and adjusting EMF 213 and/or frequency 233 can continue until the level of the operating parameter lies in the predetermined range. Although the present example refers to a predetermined range, the disclosure is not so limited, and predetermined range can be replaced by a predetermined level for the operating parameter.

In some examples, memories 213 and 217 can store secure data in secure memory arrays. For example, the secure data stored in memories 213 and 217 can be sensitive data related to the operation and/or security of device 201 and apparatus 203, respectively. The sensitive data can also include information about human 102.

A secure memory array can be assessed by secure commands upon authentication of the secure commands. In various instances, a secure array can include a secret region that cannot be accessed by the user of device 201 or apparatus 203. For example, the secret region can store remediation data that can be swapped with the secure data during a remediation process that can be performed as a result of the secure data changing as a result of a hacker attack or a technical failure in the operation of the memory.

The secure data and the remediation data can be the same when the secure data and the remediation data are in their initial state and first stored. However, the remediation data can be left unaltered (e.g., never updated) so that the remediation data remains in its initial state. For example, no operations, such as read, write, or erase operations, may be performed on the remediation data after the remediation data is stored. Alternatively, the secure data and remediation data can be updated together to have the same patterns.

In various instances, a particular cryptographic code (e.g., a secret cryptographic code) can be stored in the secret region and left unaltered for the lifetime of device 201 or apparatus 203, depending upon which of device 201 or apparatus 203 includes the secret region. For example, the particular cryptographic code can be a cryptographic hash (e.g., a hash message authentication code (HMAC)) calculated from a secret key and the secret data when the secret data is in its initial state, before any operations, such as read, write, or erase operations, have been performed. The particular cryptographic code can be compared (e.g., during an attestation procedure) to a cryptographic code calculated from the secret key secure data at a later time to validate the secure data to determine whether the secure data is still secure (e.g., has not changed as a result of a hacker attack). In some examples, the cryptographic codes to be compared to the particular cryptographic code can be commuted on a session by session basis using a different session key in place of the secret key for each session. Session keys are discussed further herein (e.g., in conjunction with FIG. 9).

Figure 3:
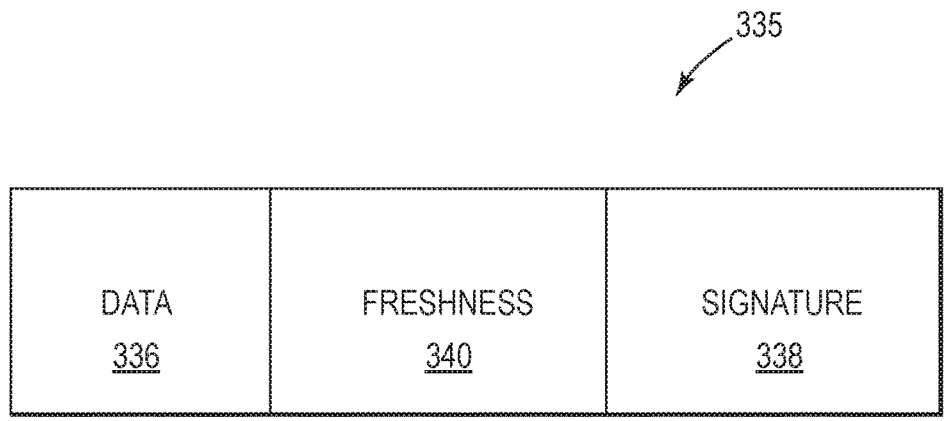
FIG. 3 illustrates an example of a secure communication in accordance with a number of embodiments of the present disclosure.

FIG. 3 illustrates an example of a secure communication, such as a secure transmission 335, in accordance with a number of embodiments of the present disclosure. For example, secure transmission 335 can include data 336 and a digital signature 338. Secure transmission 335 can also include a freshness indicator 340, such as monotonically increasing count or a NONCE (e.g., an arbitrary number that is used only once). For example, a security component, such as security component 214 or 218, can generate secure transmission 335 by generating and appending digital signature 338 to data 336 and by appending freshness indicator 340 to data 336.

Data 336 can be accessed in response to verifying digital signature 338, for example. In instances in which secure transmission 335 is generated by device 201, data 336 can include information (e.g., service information), such as the status of the charge 221 on battery 220, the status of the temperature 222 of battery 220, the status of the EMI, and/or information 223. In instances in which secure transmission 335 is generated by apparatus 203, data 336 can include service information, such as a status of EMF 231 and/or frequency 233. As discussed further herein (e.g., in conjunction with FIG. 7), a public key can be the service information. In some instances, data 336 can include a set of public security data and service information and, for example, transmission 335 can be referred to as a packed transmission.

Figure 4:
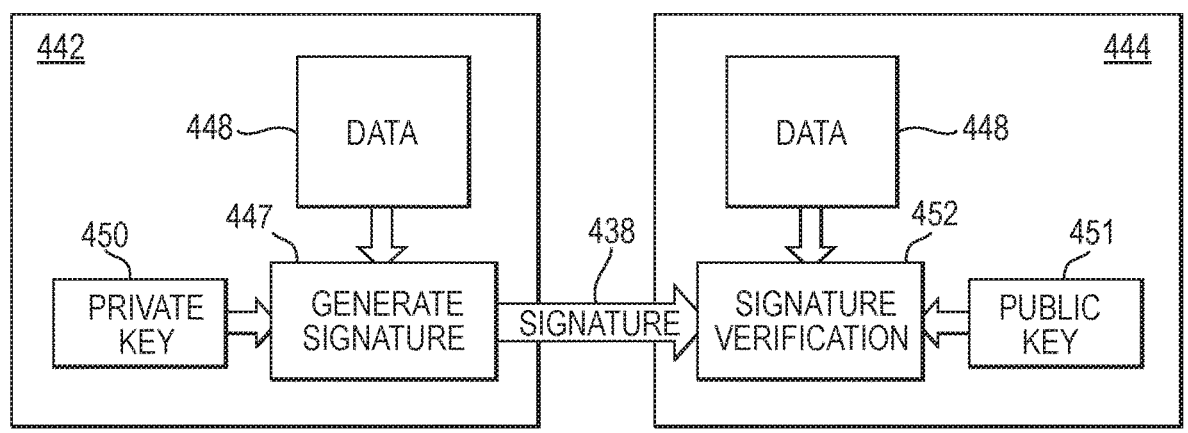
FIG. 4 illustrates an example of digital signature generation and verification in accordance with a number of embodiments of the present disclosure.

FIG. 4 illustrates an example of digital signature generation and verification in accordance with a number of embodiments of the present disclosure. In the example of FIG. 4, a transmitter 442, that can be apparatus 203 or device 201, can generate the digital signature 438 that can be digital signature 338. A receiver 444, that can be device 201 when apparatus 203 is the transmitter or apparatus 203 when device 201 is the transmitter, can determine whether digital signature 438 is authentic.

A security component of the transmitter, such as security component 214 when device 201 is transmitter 442 or security component 218 when apparatus 203 is the transmitter 442, can generate digital signature 438. A security component of the receiver, such as security component 214 when device 201 is receiver 444 or security component 218 when apparatus 203 is receiver 444, can determine whether the digital signature is authentic.

Transmitter 442 can generate digital signature 438 at block 447 by generating a cryptographic code, such as a cryptographic hash, of data 448 and encrypting the cryptographic code with a private key 450. Data 448 can be the data in a secure transmission that is to be signed by digital signature 438, such as data 336. In some examples, data 448 can also include the freshness indicator, such as freshness indicator 340, of the digital transmission.

Transmitter 442 can send digital signature 438, data 448, and a public key 451 to receiver 444. Receiver 444 can determine whether digital signature 438 is authentic by performing a signature verification procedure at block 452. For example, the signature verification procedure can include, at block 452, generating a cryptographic code of data 448, decrypting digital signature 438 with public key 451, and comparing decrypted digital signature 438 to the generated cryptographic code. If the generated cryptographic code matches the decrypted digital signature, the digital signature is authentic (e.g., valid). If the generated cryptographic code mismatches the decrypted digital signature, the digital signature is not authentic (e.g., invalid).

In some examples, receiver 444 might determine whether the freshness indicator 340 is correct by comparing freshness indicator 340 to a freshness indicator stored in a memory of receiver 444 that can be memory 213 when device 201 is receiver 444 or memory 217 when apparatus 203 is receiver 444. For example, the stored freshness indicator can be a nonce or a monotonically increasing count generated by monotonic counter of receiver 444.

If freshness indicator 340 matches the stored freshness indicator, receiver 444 may determine freshness indicator 340 is correct. If freshness indicator 340 mismatches the stored freshness indicator, receiver 444 may determine freshness indicator 340 is incorrect. In some examples, receiver 444 might perform the signature verification in response to determining that freshness indicator 340 is correct. However, receiver 444 might determine that the digital signature is not authentic in response to determining that freshness indicator 340 is incorrect without performing the signature verification procedure at block 452.

In some examples, a secure transmission can be susceptible to malicious attacks aimed at obtaining and/or altering data in the secure transmission. Such attacks can include replay attacks, for example, that can involve the malicious or fraudulent repeat or delay of the secure transmission and can involve intercepting and retransmitting the secure transmission. Verifying the freshness of a secure transmission can guard against (e.g., eliminate) the possibility of replay.

Figure 5:
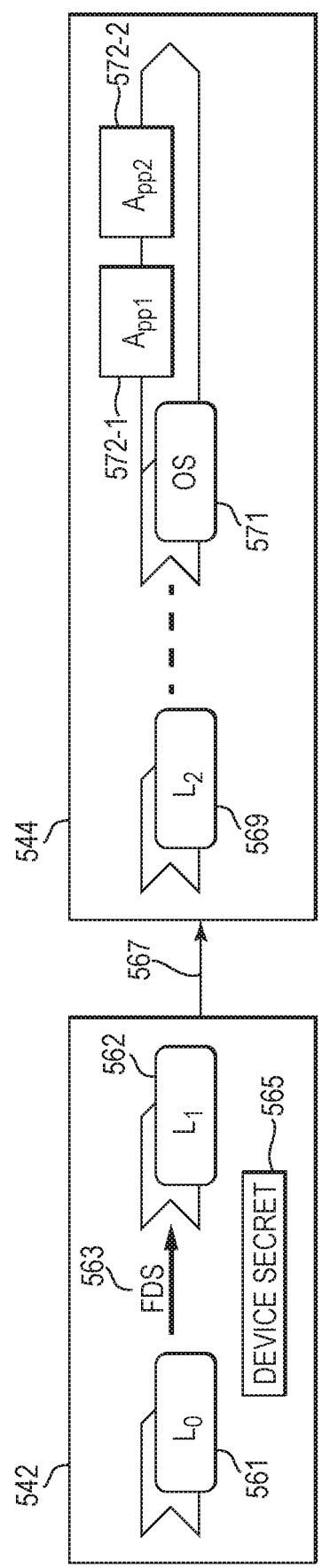
FIG. 5 is a block diagram of an example transmitter/receiver system in accordance with a number of embodiments of the present disclosure.

FIG. 5 is a block diagram of an example transmitter/receiver system in accordance with a number of embodiments of the present disclosure. For example, the system in FIG. 5 can include a transmitter 542 that can be apparatus 203 or device 201 and a receiver 544 that can be device 201 when apparatus 203 is the transmitter or apparatus 203 when device 201 is the transmitter.

The system depicted in FIG. 5 can boot in stages using layers. A layer can be served by a preceding layer and serve a subsequent layer, thereby creating an interconnected web of the layers that builds upon lower order layers and serves higher order layers. As is illustrated in FIG. 5, a layer 561, (e.g., Layer 0 ("L$_0$")) and layer 562 (e.g., Layer 1 ("L$_1$")) are within transmitter 542. For example, layers 561 and 562 can be in a security component of transmitter 542, such as security component 214 when device 201 is the transmitter 542 or security component 218 when apparatus 203 is the transmitter 542.

Layer 561 can provide a secret key, such as a Firmware Derivative Secret (FDS) key 563 to layer 562. FDS 563 can describe the identity of code of layer 562 and incorporate secret data, such as device secret 565, that can be stored in a memory of transmitter 542, such as in memory 213 when device 201 is transmitter 542 or memory 217 when apparatus 203 is transmitter 542. For example, device secret 565 can be stored in a secret region of the memory of transmitter 542 during the manufacture of transmitter 542. For example, the secret region may be inaccessible to a user of the system depicted in FIG. 5.

In an example, a particular protocol (such as robust internet of things (RIOT) core protocol) can use the FDS 563 to validate code of layer 562 that it loads. For example, the particular protocol can include a device identification composition engine (DICE) (e.g., in the security component of transmitter 542) and/or the RIOT core protocol. For example, the RIOT protocol can be stored in the memory of transmitter 542 and executed by a processor of transmitter 542, such as processor 212 when device 201 is transmitter 542 or processor 216 when apparatus 203 is transmitter 542.

As an example, an FDS can include immutable information about transmitter 542 that can include a Layer 1 firmware image itself, a manifest that cryptographically identifies authorized Layer 1 firmware, a firmware version number of signed firmware in the context of a secure boot implementation, and/or security-critical configuration settings for transmitter 542. For example, the immutable information can remain fixed for the life of transmitter 542 and can be stored in the secret region of the memory of transmitter 542. Device secret 565 and the immutable information can be used to create FDS 563 such that FDS 563 is based on device secret 565 and the immutable information.

Transmitter 542 can transmit public security data, such as security data (e.g., a set of public security parameters), as illustrated by arrow 567, to receiver 544. The transmitted set of public security parameters can include a transmitter identification, a certificate (e.g., a transmitter identification certificate), and/or a transmitter public key. A layer 569 (e.g., Layer 2 ("L$_2$")) of receiver 544 can receive the transmitted set of public security parameters and execute the set of public security parameters in operations of the operating system ("OS") 571 and on an application (App$_1$) 572-1 and application (App$_2$) 572-2.

In an example operation, transmitter 542 can read the device secret 565, hash an identity of transmitter 562 (e.g. the immutable information of transmitter 562), and perform a calculation including:

$K_{L1}$=KDF[$Fs(s)$,Hash("immutable information")]

in which $K_{L1}$ is a transmitter public key, KDF (e.g., KDF defined in the National Institute of Standards and Technology (NIST) Special Publication 800-108) is a key derivation function (e.g., HMAC-SHA256), and Fs(s) is the device secret 565.

FDS 563 can be determined by performing:

FDS=HMAC-SHA256[$Fs(s)$,SHA256("immutable information")]

Note that FDS 563 is a cryptographic code, such as a hash message authentication code (HMAC) (e.g., HMAC-SHA256), of the device secret 565 and the immutable information. As such, FDS 563 can be based on device secret 565 and the immutable information.

Figure 6:
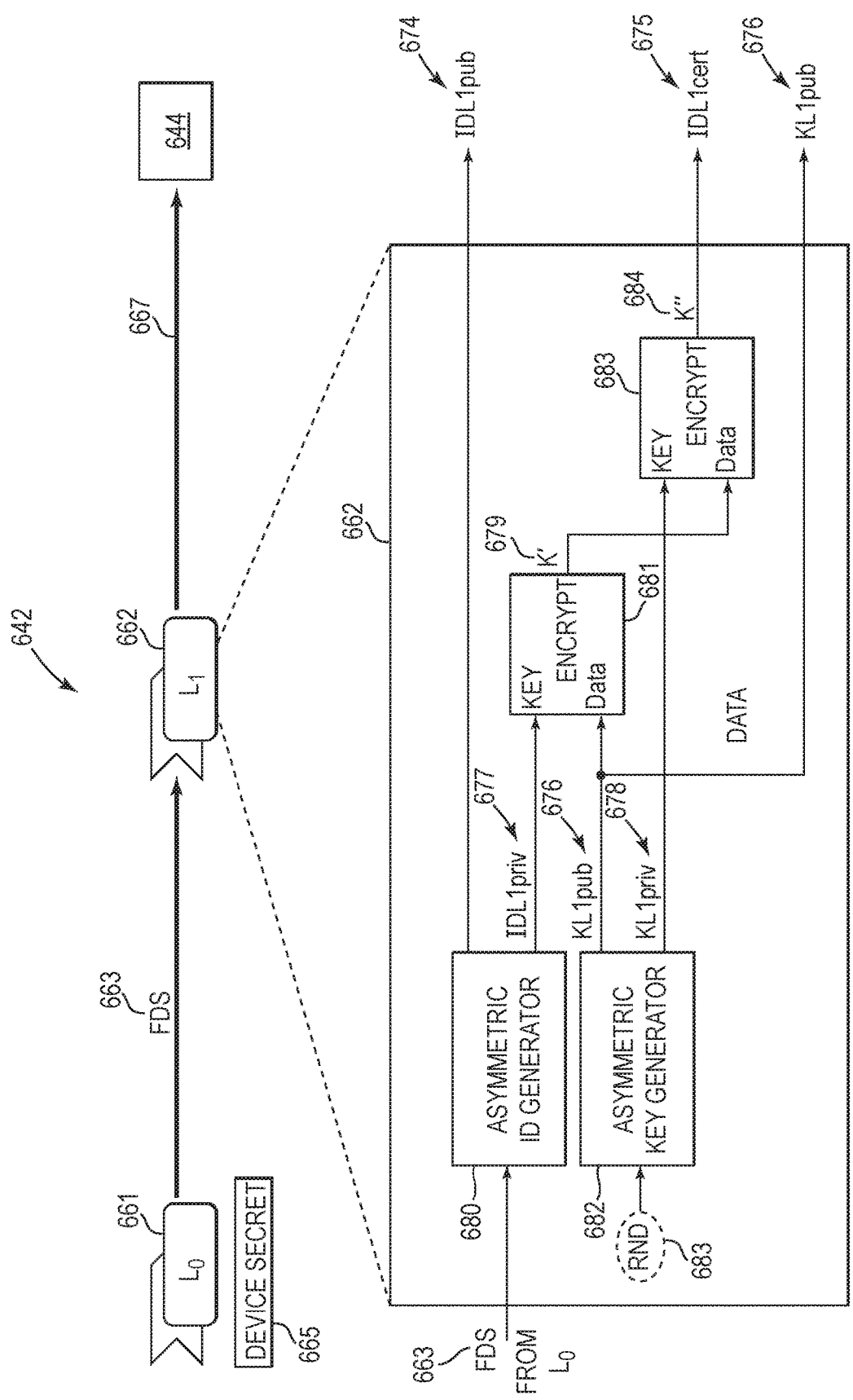
FIG. 6 is a block diagram of a transmitter in accordance with a number of embodiments of the present disclosure.

FIG. 6 is a block diagram of a transmitter 642 that can be transmitter 542 in accordance with a number of embodiments of the present disclosure. For example, FIG. 6 depicts transmitter 642 performing a process to determine a number (e.g., a set) of security parameters. A security component of transmitter 642, such as security component 214 when device 201 is the transmitter 642 or security component 218 when apparatus 203 is the transmitter 642, can include a layer 661 (e.g., layer L$_0$) that can be layer 561 and a layer 662 (e.g., layer L$_1$) that can be layer 562.

FIG. 6 is an example of a determination of transmitter security parameters, including the set public transmitter security parameters: transmitter public identification 674 (e.g., IDL1pub), transmitter identification certificate 675 (e.g., IDL1cert) of layer 662 (e.g., of transmitter 642), and transmitter public key 676 (e.g., KL1pub) and the set of private transmitter security parameters: transmitter private identification 677 (e.g., IDL1priv) and transmitter private key 678 (e.g., KL1priv). Note that "L1" in the security parameters refers to layer L1.

The set public security parameters can be openly shared and can be sent, as indicated by arrow 667, to receiver 644 that can be receiver 544 (e.g., to layer 569 of receiver 544). Transmitter public identification 674 can be used by a receiver 644 to determine an identity of transmitter 642, and receiver 644 can use identification certificate 675 to verify the identity of the transmitter 642. The private transmitter security parameters can be kept private in receiver 642.

In some examples, transmitter private key 678 can be private key 450 and can be used to encrypt the cryptographic code at block 447, as described previously in conjunction with FIG. 4. Transmitter public key 676 can be public key 451 that can be used to decrypt the cryptographic code generated at block 452, as described previously in conjunction with FIG. 4.

In some instances, data 336 can include the set public security parameters in addition to the service information described previously. In various instances, public key 676 can be the service information.

An FDS 663 (e.g., that can be FDS 563) can be sent from layer 661 to layer 662 and can be used by an asymmetric ID generator 680 to generate transmitter public identification 674 and transmitter private identification 677. The generated transmitter private identification 677 can be used as a key input into an encryptor 681. Encryptor 681 can be any processor, computing device, etc. used to encrypt data. For example, encryptor 681 can be a portion of processor 212 when device 201 is transmitter 642 or a portion of processor 216 when apparatus 203 is transmitter 642.

Layer 662 can include an asymmetric key generator 682. In some examples, a random number generator (RND) 683 can input a random number into asymmetric key generator 682. Asymmetric key generator 682 can generate transmitter public key 676 and transmitter private key 678. Transmitter public key 676 can be an input (as "data") into encryptor 681 along with transmitter private identification 677. Encryptor 683 can be any processor, computing device, etc. used to encrypt data. For example, encryptor 683 can be a portion of processor 212 when device 201 is transmitter 642 or a portion of processor 216 when apparatus 203 is transmitter 642.

Encryptor 681 can generate a result 679 (e.g., result K') of encrypting transmitter public key 676 with transmitter private identification 677. Transmitter private key 678 and result 679 can be input into an encryptor 683 resulting in an output 684 (e.g., output K") that can be the result of encrypting result 679 with transmitter private key 678. Output 684 is the transmitter identification certificate 675 that can be transmitted to layer 569.

The set of public security parameters can allow receiver 644 to authenticate transmitter 642 to receiver 644 by allowing receiver 644 to verify the identity of transmitter 642. By verifying the identity of transmitter 642, receiver 644 can be assured that various secure transmissions received by receiver 644 originated from transmitter 642. As such, receiver 644 can be assured that transmitter 642 is a trusted source of data. As an example, secure transmissions sent from transmitter 642 to receiver 644 can be associated with an identity of transmitter 642 by verifying, by receiver 644, transmitter identification certificate 675. For example, verifying transmitter identification certificate 675 at receiver 644 can authenticate transmitter 642 to receiver 644, thereby verifying transmitter 642 as a trusted source.

By verifying transmitter identification certificate 675 at receiver 644, receiver 644 can confirm that transmitter 642 includes device secret 665. As such, receiver 644 can authenticate transmitter 642 to receiver 642 by confirming that transmitter 642 includes device secret 665. Note that transmitter identification certificate 675 is based on FDS 663 that is based on device secret 665. Verification of a transmitter identification certificate is discussed further herein in conjunction with FIGS. 7 and 8.

Figure 7:
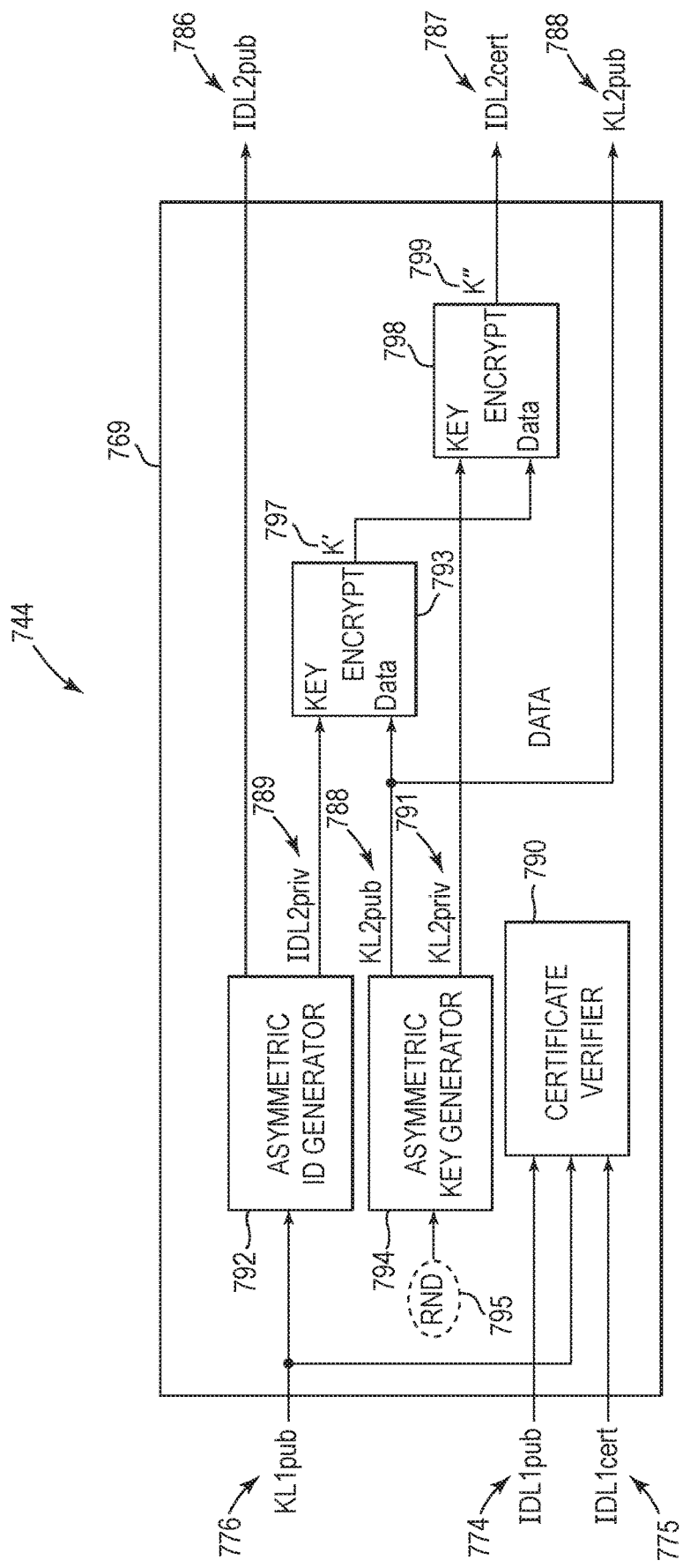
FIG. 7 is a block diagram of a receiver in accordance with an embodiment of the present disclosure.

FIG. 7 is a block diagram of a receiver 744 that can be receiver 544 or receiver 644 in accordance with a number of embodiments of the present disclosure. For example, FIG. 7 depicts receiver 744 performing a process to determine security data, such as a set of security parameters. FIG. 7 illustrates a layer 769 (e.g., Layer 2) of receiver 744. Layer 769 can be layer 569 of receiver 544, for example. A security component of receiver 744, such as security component 214 when device 201 is receiver 744 or security component 218 when apparatus 203 is receiver 744, can include layer 769.

FIG. 7 is an example of a determination of a set of receiver security parameters, including the set of public receiver security parameters: receiver public identification 786 (e.g., IDL2pub), receiver identification certificate 787 (e.g., IDL2cert) of layer 769 (e.g., of receiver 744), and receiver public key 788 (e.g., KL2pub) and the set of private transmitter security parameters: receiver private identification 789 (e.g., IDL2priv) and receiver private key 791 (e.g., KL2priv). Note that "L2" in the security parameters refers to layer L2.

In some examples, when apparatus 203 is acting as receiver 744, apparatus 203 can send public key 788 to device 201, so device 201 can encrypt data, such as data 336 in secure transmission 335, using public key 788 and can send encrypted data 336 to apparatus 203. Apparatus 203 can then use private key 791 to decrypt encrypted data 336 in response to verifying the identity of device 201 and authenticating digital signature 338.

Similarly, for example, when device 201 is acting as receiver 744, device 201 can send public key 788 to apparatus 203, so apparatus 203 can encrypt data, such as data 336 in secure transmission 335, using public key 788 and can send encrypted data 336 to device 201. Device 201 can then use private key 791 to decrypt encrypted data 336 in response to verifying the identity of apparatus 203 and authenticating digital signature 338.

In various examples, such as examples in which transmission 335 is a packed transmission, the data 336 in FIG. 3 can include the service data discussed in conjunction with FIG. 3 and the set of public receiver security parameters (e.g., receiver public identification 786, receiver identification certificate 787, and receiver public key 788). For example, when apparatus 203 is acting as receiver 744, apparatus 203 can send a respective packed transmission 335 back to device 201 when device 201 is acting as transmitter 642, and when device 201 is acting as receiver 744, device 201 can send a respective packed transmission 335 back to apparatus 203 when apparatus 203 is acting as transmitter 642. As such, apparatus 203 and device 201 can exchange the respective packed transmissions 335.

In some instances, public key 788 of the set of public receiver security parameters in data 336 of transmission 335 can be the service information, and the exchanged transmissions can be used to generate additional transmissions. For example, device 201 can generate an additional transmission (with additional services) from the transmission 335 received at device 201 and including the set of public receiver security parameters from apparatus 203, according to the example in FIG. 7, with the set of public receiver security parameters from apparatus 203 as inputs. Similarly, for example, apparatus 203 can generate an additional transmission (with additional services) from the transmission 335 received at apparatus 203 and including the set of public receiver security parameters from device 201, according to the example in FIG. 7, with the set of public receiver security parameters from apparatus 201 as inputs. As such, additional services can be added, for example.

Receiver public identification 786 can be used by a next higher order layer than layer 769, such as, for example, a layer 3 (not shown), to determine an identity of layer 769. Layer 3 can use identification certificate 787 to verify the identity of layer 769.

In some examples, apparatus 203 and device 201 can exchange a set of public security parameters during a mutual authentication process. For example, during the mutual authentication process, apparatus 203, acting as transmitter 642, can send a set of transmitter public security parameters to device 201, acting as receiver 744, and device 201, acting as transmitter 642, can send a set of transmitter public security parameters to apparatus 203, acting as receiver 744. In the example of FIG. 7, such a set of transmitter public security parameters can include: transmitter public key 776 (e.g., KL1pub) that can be transmitter public key 676, transmitter public identification 774 (e.g., IDL1pub) that can be transmitter public identification 674, and transmitter identification certificate 775 (e.g., IDL1cert) that can be transmitter identification certificate 675.

Layer 769 can include a certificate verifier 790 that can receive the set of transmitter public security parameters from transmitter 642, for example. Certificate verifier 790 can determine whether transmitter 642 is authentic (e.g., verify the identity of transmitter 642) by determining whether transmitter identification certificate 776 valid, and thereby determine whether transmitter 642 is trusted. For example, certificate verifier 790 can authenticate transmitter 642 to receiver 744, and thus verify the identity of transmitter 642, in response to verifying transmitter identification certificate 776. Receiver 744 can determine, in response to transmitter identification certificate 776 being verified or not being verified, whether to accept or ignore secure transmissions received from transmitter 642. Further details of verifying identification certificate 776 are further described herein (e.g., in connection with FIG. 8).

Note that security component 214 of device 210 and security component 218 of apparatus 203 can each include a certificate verifier, such as certificate verifier 790. In an example, while apparatus 203 and device 201 are performing the mutual authentication process, the certificate verifier of apparatus 203 can verify a transmitter identification certificate, such as transmitter identification certificate 776, from device 201 to authenticate device 201 to apparatus 203, and the certificate verifier of device 201 can verify a transmitter identification certificate, such as transmitter identification certificate 776, from apparatus 203 to authenticate apparatus 203 to device 201.

Transmitter public key 775 can be used by an asymmetric ID generator 792 of receiver 744 to generate receiver public identification 786 and receiver private identification 789. Receiver public identification 786 is illustrated as shared by the arrow extending to the right and outside layer 769. The generated private identification 789 is used as a key input into an encryptor 793. Encryptor 793 can be any processor, computing device, etc. used to encrypt data. For example, encryptor 793 can be a portion of processor 212 when device 201 is receiver 744 or a portion of processor 216 when apparatus 203 is receiver 744.

Layer 769 can include an asymmetric key generator 794. In some examples, a random number generator (RND) 795 can input a random number into asymmetric key generator 794. Asymmetric key generator 794 can generate receiver public key 788 and receiver private key 791. Receiver public key 788 can be an input (as "data") into an encryptor 793. Encryptor 793 can generate a result 797 (e.g., a result K') using the inputs: receiver private identification 789 and receiver public key 788. Receiver private key 791 can be input into an encryptor 798, and result 797 can be input (as "data') into encryptor 798, resulting in an output 799 (e.g., output K") that is receiver identification certificate 787. Encryptor 798 can be any processor, computing device, etc. used to encrypt data. For example, encryptor 798 can be a portion of processor 212 when device 201 is receiver 744 or a portion of processor 216 when apparatus 203 is receiver 744.

Figure 8:
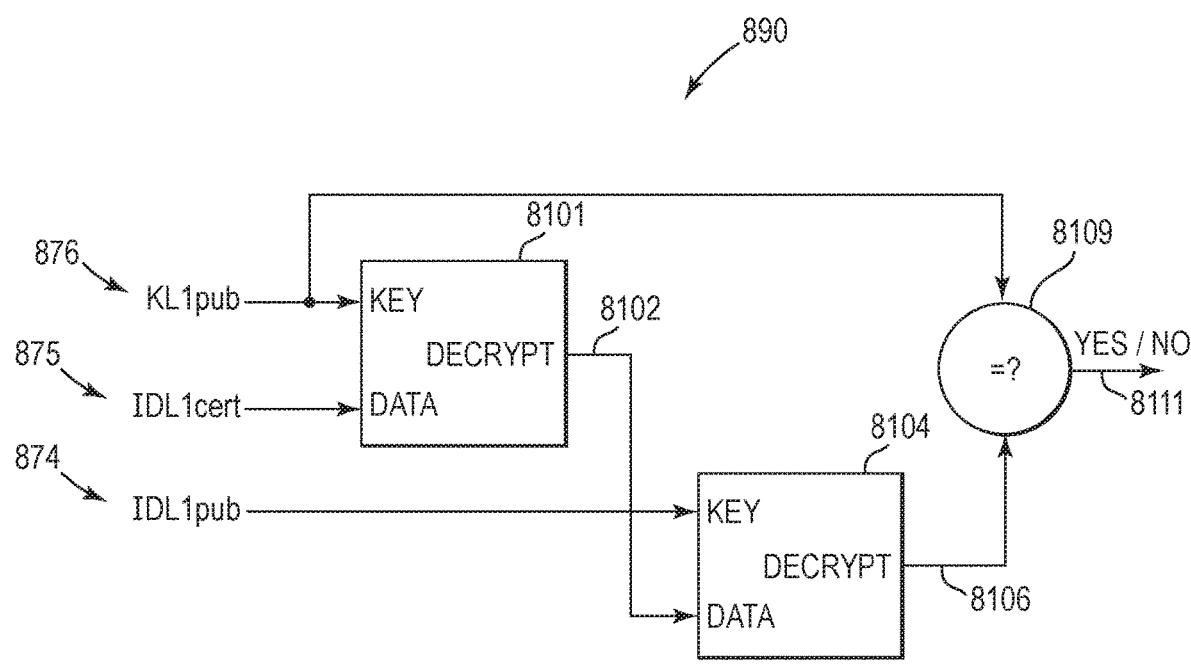
FIG. 8 is a block diagram of an example of a certificate verifier in accordance with a number of embodiments of the present disclosure.

FIG. 8 is a block diagram of an example of certificate verifier 890 that can be certificate verifier 790 in accordance with a number of embodiments of the present disclosure. For example, certificate verifier 890 can be a portion of layer 769 of receiver 744.

Certificate verifier 890 can receive a set of transmitter public security parameters (e.g., from layer 662 of transmitter 642), including a transmitter public key 876 (e.g., KL1pub) that can be transmitter public key 676, transmitter public identification 874 (e.g., IDL1pub) that can be transmitter public identification 674, and transmitter identification certificate 875 (e.g., IDL1cert) that can be transmitter identification certificate 675. Certificate verifier 890 can determine whether the identity of transmitter 642 is valid based on the set of transmitter public security parameters, and thereby determine whether transmitter 642 is trusted.

Transmitter public key 876 can be input into a decryptor 8101 and transmitter identification certificate 875 can be input (as "data") into decryptor 8101. Decryptor 8101 can be any processor, computing device, etc. used to decrypt data. For example, decryptor 8101 can be a portion of processor 212 when device 201 is a receiver, such as receiver 744, or a portion of processor 216 when apparatus 203 is a receiver, such as receiver 744.

A result 8102 of the decryption of transmitter identification certificate 875 with transmitter public key 876 can be used as a data input into a decryptor 8104 along with transmitter public identification 874. A result 8106 of the decryption of result 8102 with transmitter public identification 874 can be compared, by a comparator 8109, to transmitter public key 876 to determine whether transmitter identification certificate 876 is valid. Decryptor 8104 can be any processor, computing device, etc. used to decrypt data. For example, decryptor 8104 can be a portion of processor 212 when device 201 is a receiver, such as receiver 744, or a portion of processor 216 when apparatus 203 is a receiver, such as receiver 744.

A match between result 8106 and transmitter public key 876 verifies identification certificate 875 and determines that identification certificate 875 is valid, whereas a mismatch between result 8106 and transmitter public key 876 determines that identification certificate 875 is invalid and not verified. A match between result 8106 and transmitter public key 876 can cause comparator 8109 to generate an output 8111 of "yes," indicating that, yes, identification certificate 875 is verified. A mismatch between result 8106 and transmitter public key 876 can cause comparator 8109 to generate an output 8111 of "no," indicating that, no, identification certificate 875 not verified (invalid).

The verification of identification certificate 875 can authenticate transmitter 642 to receiver 744, and thus verify the identity of transmitter 642 to receiver 744, as described previously. For example, verification of identification certificate 875 can verify that transmitter 642 includes device secret 665, and thus that transmitter 642 is trusted.

Figure 9:
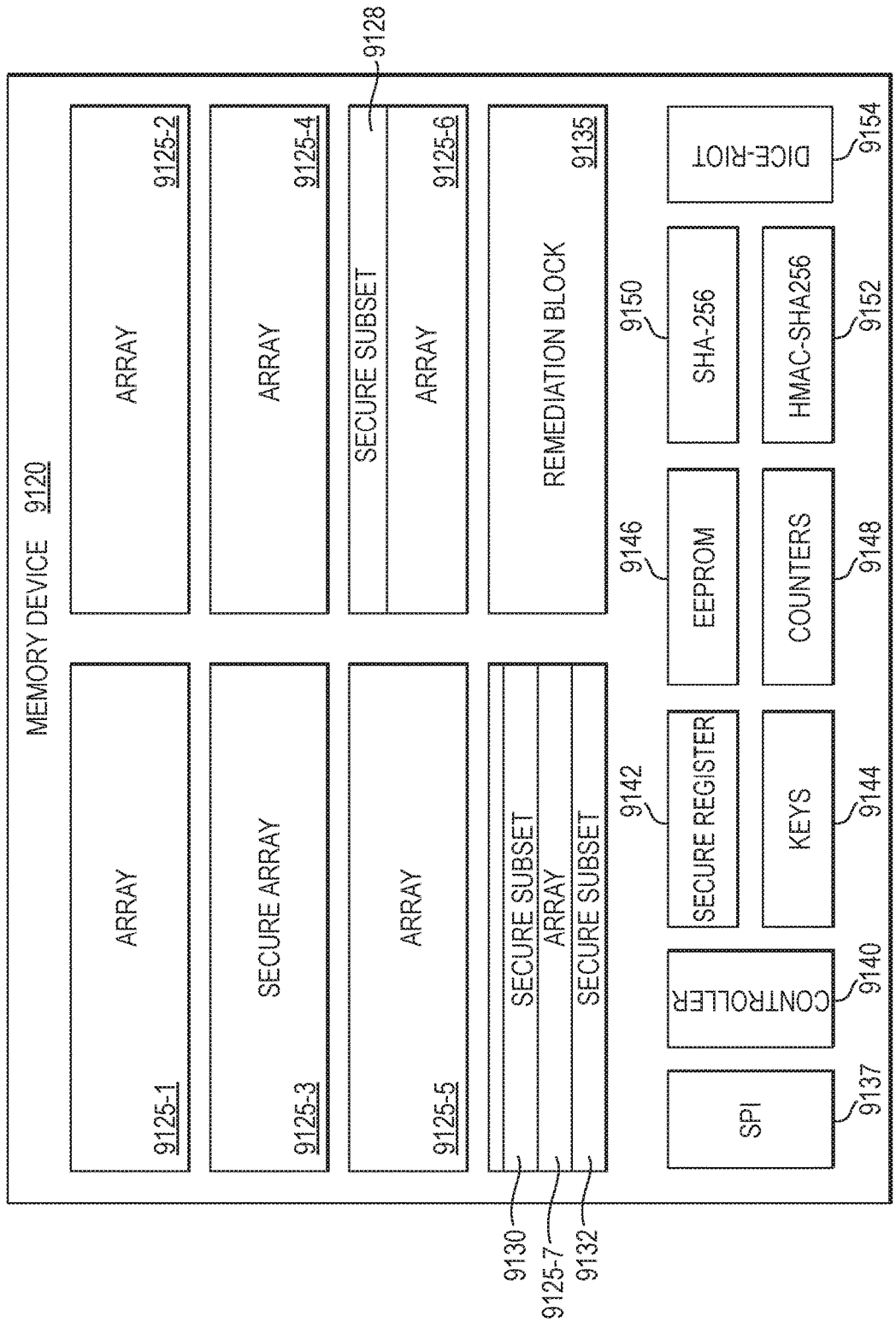
FIG. 9 is a block diagram of an example of a memory device in accordance with a number of embodiments of the present disclosure.

FIG. 9 is a block diagram of an example of a memory device 9120 that can be a portion of memory 213 or memory 217 in accordance with a number of embodiments of the present disclosure. Memory device 9120 can include a number of memory arrays 9125-1 through 9125-7. Memory array 9125-3 is a secure array. A subset 9128 of memory array 9125-6 includes a secure array, and subsets 9130 and 9132 of memory array 9125-7 include a secure array. Subsets 9128, 9130, and 9132 can each include, for instance, 4 kilobytes of data. However, embodiments of the present disclosure are not limited to a particular number or arrangement of memory arrays or secure arrays. In various examples, the secure arrays can be as described previously in conjunction with FIG. 2.

Memory device 9120 can include a remediation (e.g., recovery) block 9135. Remediation block 9135 can be used as a source of data (e.g., remediation data, as described previously) as a result of the data in the secure arrays changing as a result of a hacker attack or a technical failure in the operation of memory device 9120. Remediation block 9135 can be outside of the area of memory device 9135 that is addressable by a host, such as processor 212 or 216. Although shown as a separate block, remediation block 9135 is not so limited and can be a secret region in a secure array, as described previously.

Memory device 9120 can include a serial peripheral interface (SPI) 9137 and a controller 9140. Memory device 9120 can use SPI 9137 and controller 9140, such as control circuitry, to communicate with the host and memory arrays 9125-1 through 9125-7.

Memory device 9120 can include a secure register 9142 for managing the security of memory device 9120. For example, secure register 9142 can configure, and communicate externally with, an application controller. Further, secure register 9142 can be modifiable by an authentication command.

In some examples, processor 212 or 216 can act as an application controller when memory device 9120 is a portion of memory 213 or 217. In other examples, memory device 9120 can be a component of device 201 and can be coupled to computing device 205 (e.g., that can act as the application controller). Memory device 9120 can be a component of 203, for example, and can be coupled to computing device 208 (e.g., that can act as the application controller).

Memory device 9120 can include keys 9144. For instance, memory device 9120 can include eight different slots to store keys, such as secret (e.g., root) keys, DICE-RIOT keys, and/or other external session keys. For example, keys 9144 can be included in a security component, such as security component 214 or 218 when security component 214 or 218 can be in memory 213 or 217 and memory device 9120 can be a portion of memory 213 or 217.

Session keys can be used in place of a secret key that can be stored in a secret region of a secure array. For example, a new (e.g., different) session key can be used during each power cycle of memory device 9120 that can start at each power-up (e.g., reset) of memory device 9120. A session key can be calculated, for example, for a power cycle at the end of the preceding power cycle by security component 214 or 218. For example, the session key can be a message authentication code (MAC) of the secret key and a monotonic count at the end of the preceding power cycle. Alternatively, a session key can be an HMAC of the secret key and the monotonic count, for example.

Memory device 9120 can include an electronically erasable programmable read-only memory (EEPROM) 9146. EEPROM 9146 can provide a secure non-volatile area available for the host, in which individual bytes of data can be erased and programmed.

Memory device 9120 can include counters (e.g., monotonic counters) 9148. For instance, memory device 9120 can include six different monotonic counters, two of which may, for example, be included in security component 214 or 216, and may be used for the freshness of secure transmissions, such as freshness 340 of secure transmission 335 or in the generation of the session keys, and four of which may be used by the host.

Memory device 9120 can include (e.g., as a portion of security component 214 or 216) a SHA-256 cryptographic hash engine 9150 and/or an HMAC-SHA-256 cryptographic hash engine 9152. SHA-256 cryptographic hash engine 9150 and/or an HMAC-SHA-256 cryptographic hash engine 9152 can be used by security component 214 or 216 to generate cryptographic hashes, such as, for instance, the cryptographic hashes described previously herein, and/or a secret (e.g., golden) hash that can used to validate data stored in memory arrays 9125-1 through 9125-7 (e.g., such as part of the attestation procedure described previously). The golden hash can, for example, be stored in inaccessible portion a secure memory array, such as in a secret portion of secure array 9125-3, and can be used during the process of validating the data of the secure array.

For example, a run-time cryptographic hash can be generated (e.g., calculated), and compared with the golden hash. If the comparison indicates the run-time and golden hashes match, it can be determined that the secure array has not been altered, and therefore the data stored therein is valid. If, however, the comparison indicates the run-time and golden hashes do not match, this may indicate that the data stored in the secure array has been changed (e.g., due to a hacker or a fault in the memory), and this can be reported to the host.

Further, memory device 9120 can support layers L0 and L1 of DICE-RIOT 9154 that can be a portion of security component 214 or 216.

In the preceding detailed description, reference is made to the accompanying drawings that form a part hereof, and in which is shown, by way of illustration, specific examples. In the drawings, like numerals describe substantially similar components throughout the several views. Other examples may be utilized, and structural, logical and/or electrical changes may be made without departing from the scope of the present disclosure.

The figures herein follow a numbering convention in which the first digit or digits correspond to the drawing figure number and the remaining digits identify an element or component in the drawing. Similar elements or components between different figures may be identified by the use of similar digits. As will be appreciated, elements shown in the various embodiments herein can be added, exchanged, and/or eliminated so as to provide a number of additional embodiments of the present disclosure. In addition, as will be appreciated, the proportion and the relative scale of the elements provided in the figures are intended to illustrate the embodiments of the present disclosure and should not be taken in a limiting sense.

As used herein, "a," "an," or "a number of" something can refer to one or more of such things. A "plurality" of something intends two or more. As used herein, the term "coupled" can include electrically coupled, directly coupled, and/or directly connected with no intervening elements (e.g., by direct physical contact), indirectly coupled and/or connected with intervening elements, or wirelessly coupled. The term coupled may further include two or more elements that co-operate or interact with each other (e.g., as in a cause and effect relationship).

Although specific examples have been illustrated and described herein, those of ordinary skill in the art will appreciate that an arrangement calculated to achieve the same results can be substituted for the specific embodiments shown. This disclosure is intended to cover adaptations or variations of one or more embodiments of the present disclosure. It is to be understood that the above description has been made in an illustrative fashion, and not a restrictive one. The scope of one or more examples of the present disclosure should be determined with reference to the appended claims, along with the full range of equivalents to which such claims are entitled.

What is claimed is:

1. An apparatus, comprising:
a computing component;
wherein the computing component is configured to:
receive a wireless transmission from an implanted device, wherein the wireless transmission comprises a digital signature;
verify an identity of the implanted device by verifying security data from the implanted device, wherein verifying the security data comprises verifying that the implanted device comprises particular secret data stored in a secret region of a memory of the implanted device that is inaccessible to both a user and a processor of the apparatus; and
perform an authentication procedure, in response to verifying the identity of the implanted device, to determine whether the transmission is authentic by determining whether the digital signature is authentic.

2. The apparatus of claim 1, wherein the computing component is configured to ignore the received transmission in response to the computing component being unable to verify the identity of the implanted device.

3. The apparatus of claim 1, wherein the computing component is configured to:
generate a code from the particular secret data and a hash of immutable information about the apparatus;
generate security data from the code; and
send the security data to the implantable device.

4. The apparatus of claim 3, wherein the code is a hash message authentication code.

5. The apparatus of claim 1, wherein the computing component is configured to determine whether the digital signature is authentic by:
generating a cryptographic code of data received from the implanted device;
decrypting the digital signature with a key received from the implanted device, and
comparing the decrypted digital signature to the generated cryptographic code to determine whether the decrypted digital signature matches the generated cryptographic code.

6. The apparatus of claim 1, wherein the computing component is configured to perform the authentication procedure in response to determining that the transmission is fresh.

7. The apparatus of claim 1, wherein
the transmission comprises encrypted information; and
the computing component is configured decrypt the information using a private key.

8. The apparatus of claim 1, wherein:
the transmission comprises data indicating that the implanted device needs to be charged; and
the apparatus is configured to wirelessly charge the implanted device in response to the computing component determining that the digital signature is authentic.

9. The apparatus of claim 1, wherein the transmission comprises a status of a number of operating parameters of the implanted device.

10. The apparatus of claim 1, wherein:
the wireless transmission received from the implanted device comprises information about the implanted device; and
the computing component is configured to receive the wireless transmission from the implanted device in response to:
the computing component transmitting a digitally signed wireless transmission to the implanted device requesting the information.

11. The apparatus of claim 1, wherein the computing component is configured to receive security data from the implanted device and to generate another set of security data from the received security data.

12. An apparatus, comprising:
a processor;
an apparatus communication component coupled to the processor;
a security component coupled to the processor; and
a power transmitter coupled to the processor;
wherein the apparatus communication component is configured to receive a wireless transmission from an implanted device;
wherein the wireless transmission comprises data indicating that the implanted device needs to be charged and a digital signature;
wherein the security component is configured to verify the digital signature;
wherein the security component is configured to verify an identity of the implanted device by verifying security data from the implanted device, wherein verifying the security data comprises verifying that the implanted device comprises particular secret data stored in a secret region of a memory of the implanted device that is inaccessible to both a user and the processor of the apparatus; and
wherein the processor is configured to cause the power transmitter to charge the implanted device by causing the power transmitter to wirelessly transmit power to the implanted device in response to the security component verifying the digital signature.

13. The apparatus of claim 12, wherein the security component is configured to verify the digital signature in response to verifying the identity of the implanted device.

14. A method, comprising:
receiving a wireless transmission at an implanted device from an apparatus, wherein the wireless transmission comprises a digital signature and data;
authenticating the received wireless transmission by verifying the digital signature;
accessing the data in response to authenticating the wireless transmission; and
receiving power wirelessly from the apparatus; and
charging the implanted device with the received power in response to the accessed data indicating that the implanted device needs to be charged; and
storing, in a secret region of a memory of the implanted device that is inaccessible to both a user and a processor of the apparatus, particular secret data; and
sending, from the apparatus to the implanted device, security data for verifying an identity of the implanted device by verifying the security data, wherein verifying the security data comprises verifying that the implanted device comprises the particular secret data stored in the secret region of the memory of the implanted device.

15. The method of claim 14, further comprising:
generating a code from the particular secret data and a hash of immutable information about the implanted device;
generating security data from the code; and
sending the security data to the apparatus.

16. The method of claim 14, further comprising verifying an identity of the apparatus by verifying additional security data from the apparatus.

17. The method of claim 16, further comprising authenticating the received wireless transmission in response to verifying the additional security data from the remote device.

18. The method of claim 14, further comprising:
establishing secure communication between the implanted device and the apparatus; and
receiving the wireless transmission at the implanted device from the remote device in response to establishing the secure communication between the implanted device and the apparatus.

19. A system, comprising:
a wireless charger; and
a wireless implanted device;
wherein the wireless implanted device is configured to authenticate the wireless charger to the wireless implanted device and the wireless charger is configured to authenticate the wireless implanted device to the wireless charger to establish secure communication between the wireless implant and the wireless charger; and
wherein the wireless charger is configured to, in response to the establishment of the secure communication between the wireless implanted device and the wireless charger:
accept a secure transmission from the wireless implanted device, indicating that the wireless implant needs to be charged, wherein the secure transmission is signed with a digital signature and includes security data from the wireless implanted device;
verify an identity of the wireless implanted device by verifying the security data from the wireless implanted device;
wherein verifying the security data comprises verifying that the wireless implanted device comprises particular secret data stored in a secret region of a memory of the wireless implanted device that is inaccessible to both a user and a processor of the wireless charger; and
wirelessly charge the wireless implanted device in response to authenticating the digital signature and verifying the security data from the wireless implanted device.

20. The system of claim 19, wherein:
the wireless implanted device is configured to send a secure transmission comprising a status of a charging parameter of the wireless implanted device; and
the wireless charger is configured to adjust its operation in response to authenticating the secure transmission.

21. The system of claim 20, wherein the charging parameter comprises electromagnetic interference sensed by the wireless implanted device, a temperature of a battery of the wireless implanted device, or an amount of charge on the battery.

22. The system of claim 19, wherein
the wireless implanted device is configured to authenticate the wireless charger to the wireless implanted device by verifying that security data from the wireless charger is based on particular secret wireless charger data; and
the wireless charger is configured to authenticate the wireless implanted device to the wireless charger by verifying that the security data from the wireless implanted device is based on particular secret wireless implanted device data.

23. The system of claim 22, wherein the particular secret wireless charger data and the particular secret wireless implanted device data are a same data.

24. The system of claim 19, wherein the wireless implanted device is a prosthesis.

* * * * *